United States Patent [19]

Day

[11] Patent Number: 5,496,959
[45] Date of Patent: Mar. 5, 1996

[54] PREPARATION OF N-ACYL TAURATES

[75] Inventor: James F. Day, Charlotte, N.C.

[73] Assignee: Hoechst Celanese Corporation, Somerville, N.J.

[21] Appl. No.: 247,920

[22] Filed: May 23, 1994

[51] Int. Cl.$^6$ ................................................. C07C 231/00
[52] U.S. Cl. ............................................ 554/69; 554/49
[58] Field of Search ........................................ 554/49, 69

[56] References Cited

U.S. PATENT DOCUMENTS

| | | | |
|---|---|---|---|
| Re. 23,823 | 5/1954 | Molteni et al. | 260/400 |
| 2,857,370 | 10/1958 | Sunberg | 260/97.5 |
| 2,880,219 | 3/1959 | Bernette et al. | 260/401 |
| 2,974,153 | 3/1961 | Gajewski et al. | 260/401 |
| 2,974,154 | 3/1961 | Schenck | 260/401 |
| 3,150,156 | 9/1964 | Lamberti | 260/401 |
| 3,232,968 | 2/1966 | Schenck et al. | 260/401 |
| 3,234,247 | 2/1966 | Abend et al. | 260/401 |
| 3,420,857 | 1/1969 | Holland et al. | 260/400 |
| 3,420,858 | 1/1969 | McCrimlisk | 260/400 |
| 3,429,136 | 2/1969 | Holt et al. | 62/114 |
| 3,745,181 | 7/1973 | Wrigley et al. | 260/400 |
| 4,092,259 | 5/1978 | Prince | 252/117 |
| 4,096,082 | 6/1978 | Prince | 252/117 |
| 4,100,097 | 6/1978 | O'Roark | 252/145 |
| 4,151,105 | 4/1979 | O'Roark | 252/145 |
| 4,234,464 | 11/1980 | Morshauser | 252/544 |
| 4,369,144 | 1/1983 | Lamberti et al. | 260/513 |
| 4,405,526 | 9/1983 | Lamberti et al. | 260/400 |
| 4,515,721 | 5/1985 | Login et al. | 143/90 |
| 4,536,338 | 8/1985 | Urban et al. | 260/400 |
| 5,041,233 | 8/1991 | Kutny | 252/121 |
| 5,300,665 | 4/1994 | Tracy et al. | 554/49 |

FOREIGN PATENT DOCUMENTS

| | | |
|---|---|---|
| 3442579 | 5/1986 | Germany. |
| 3616843 | 11/1987 | Germany. |
| 4400329.3 | 3/1994 | Germany. |
| 5222395 | 8/1993 | Japan. |

OTHER PUBLICATIONS

Petter, P., "Fatty Acid Sulphoalkyl Amides and Esters as Cosmetic Surfactants," *International Journal of Cosmetic Science*, vol. 6, pp. 249–260 (1984).

Bistline, R. G., et al., "Surface Active Agents from Isopropenyl Esters: Acylation of Isethionic Acid and N–Methyltaurine", *Journal of American Oil Chemists Society*, vol. 48, pp. 657–660 (Nov.1971).

*Detergent Analysis–A Handbook for the Cost–Effective Quality Control*, by B. M. Milwidsky and D. M. Gabriel (George Goodwin, London, 1982), pp. 119–120, 133–134, and 255–256.

*Hawley's Condensed Chemical Dictionary* (11th Edition 1987), by N. Irving Sax p. 873.

Primary Examiner—José G. Dees
Assistant Examiner—Deborah D. Carr
Attorney, Agent, or Firm—Rosemary M. Miano

[57] ABSTRACT

This invention relates to the preparation of N-acyl taurates by the direct condensation of carboxylic acids with taurate (substituted 2-aminoalkane sulfonic acids and their alkali metal salts) derivatives.

3 Claims, No Drawings

PREPARATION OF N-ACYL TAURATES

BACKGROUND OF THE INVENTION

This invention relates to the preparation of N-acyl taurates by the direct condensation of carboxylic acids with taurate (substituted 2-aminoalkane sulfonic acids and their alkali metal salts) derivatives. The compositions made by this invention are useful as wetting agents, cleansing agents, and dispersants and may be used in a wide variety of products for detergent and personal care uses such as shampoos, lotions, bubble baths, and toilet soaps.

The reaction of acid chlorides of carboxylic acids with 2-amino- or 2-hydroxyalkanesulfonic acids and their alkali metal salts to yield anionic surfactants (for example, sodium N-acyltaurates and sodium acylisethionates, respectively) is well known as the Schotten-Baumann synthesis. The products formed by this chemistry are commercially sold by Hoechst Aktiengesellschaft (Frankfurt, Germany) and Hoechst Celanese Corporation (Somerville, N.J.) as Hostapon™, and by Rhône-Poulenc (France) as Igepon™.

The Schotten-Baumann chemistry is very laborious and costly, requiring the handling of hazardous raw materials such as phosphorus trichloride and intermediates like acid chlorides as well as wastes like phosphorus acid. Large quantities of waste products are generated as a result of this chemistry. Also, the finished products contain significant amounts of sodium chloride as an undesirable by-product. The removal of the sodium chloride is possible, but expensive.

Sodium acylisethionate synthesis, pioneered by Lever Brothers, have been vastly improved by the direct esterification of fatty acids with sodium isethionate. See, for example, U.S. Pat. Nos. 4,369,144 and 4,405,526 to Lamberti et al., U.S. Pat. No. 4,536,338 to Urban et al. and U.S. Pat. No. 3,420,857 to Holland et al. This direct esterification route is cost-effective and these products are suitable for use in commercial toilet soap preparations.

Hoechst Celanese Corporation has developed improved technology to prepare sodium acylisethionates by direct esterification. Improvements in process technology include those described in co-pending application Ser. No. 07/934,062.

A variety of ways of making these compounds has been described in the art. U.S. Pat. No. 3,420,857 to Holland et al. and U.S. Pat. No. 3,420,858 to McCrimlisk disclose methods for the formation of fatty esters of hydroxysulfonates to obtain products which have reduced amounts of esters of higher molecular weight fatty acids and unreacted lower molecular weight fatty acids. The methods comprise continuously supplying to the reaction vessel, fatty acid reactants of a composition corresponding to fatty acids volatilized during the course of the reaction (in order to reduce the proportion of esters of relatively higher molecular weight fatty acids) and utilizing an improved stripping process to reduce the lower molecular weight fatty acid content. The method includes heating a mixture of an hydroxyalkylsulfonate and fatty acids to a temperature between about 390 degrees F. and 500 degrees F. (about 199–260 degrees C.). The examples are run at temperatures of at least 450 degrees F. (about 232 degrees C.). These patents note that temperatures below 450 degrees F. significantly reduce reaction rates. These patents also list a number of reaction promoters for the direct esterification reaction, including salts of strong acids and weak bases, zinc oxide and magnesium oxide, and acids and acid formers.

U.S. Pat. No. 3,429,136 to Holt et al. discloses a method for making esters of hydroxysulfonates in which the hot hydroxy-sulfonate esters are cooled from temperatures on the order of 350 degrees F. to 500 degrees F. (about 177–260 degrees C.), which are encountered in the preparation of such compounds, to a temperature below about 330 degrees F. (about 165.6 degrees C.). At this point the reaction is quenched by injecting cold water. The patent states that this quenching method is carried out without detectable amounts of hydrolysis.

U.S. Pat. No. 3,745,181 to Wrigley et al. discloses the preparation of 2-sulfoethyl esters of a number of fatty acids by acylating the sodium isethionate with the corresponding isopropenyl fatty ester by a transesterification reaction. The patent states that high purity products may be obtained using reaction times of 10–90 minutes and temperatures from 125–200 degrees C. Examples run at less than 200 degrees C., however, seem to result in decreased yields.

U.S. Pat. No. 4,405,526 to Lamberti et al. discloses a method for producing directly esterified fatty acylisethionates having a yellowness index less than about 6.0. The process consists essentially of reacting a fatty acid with an alkali metal isethionate in the presence of a catalyst comprising a mixture of zinc oxide (ZnO) and an organic sulfonic acid wherein the molar ratio of ZnO to organic sulfonic acid is about 1:1.7 or less and heating the reaction at about 200 degrees C. to about 225 degrees C until the desired product is formed.

U.S. Pat. No. 4,515,721 to Login et al. discloses a process for the production of fatty acid esters of hydroxyalkyl sulfonate salts wherein the method comprises a) heating an excess of the fatty acids with the sulfonate until the water of condensation is removed; b) quenching the crude ester by immersion in an excess of cooled liquid in which the ester product is insoluble but in which unreacted, excess fatty acids are soluble; and c) filtering the slurry to separate the relatively pure ester. Isopropanol is taught as the preferred quenching liquid, but fatty alcohols (such as stearyl alcohol), fatty alcohol ethoxylates, polyethyleneglycols, fatty triglycerides (such as tallow or hydrogenated tallow), fatty esters and paraffins may also be used as the quenching liquid. The patent notes that the presence of a certain amount of such quenching liquids is acceptable and may actually facilitate detergent formulations. The method of this patent recites a temperature range of 200–250 degrees C., but all of the examples appear to be run at 250 degrees C.

U.S. Pat. No. 4,536,338 to Urban et al. discloses a method for preparing fatty acid isethionate soaps through direct esterification wherein the catalyst is quenched by an alkaline compound at the end of the esterification to inhibit transesterification between isethionate and later added stearic acids. The method comprises a) heating a mixture of $C_6$–$C_{19}$ monocarboxylic acids with an hydroxysulfonate in the presence of a catalyst such as acidified zinc oxide, strong acids or soluble zinc salts; b) removing the liberated water; c) quenching the catalyst with an alkaline compound; and d) adding a higher molecular weight $C_{15}$–$C_{24}$ fatty acid to the reaction mixture. The patent recites a reaction temperature of between 200 degrees C. and 260 degrees C. with 233 degrees C. being standard. The patent also mentions that increasing levels of zinc oxide to achieve faster rates of reaction gives a gritty feel to toilet bars made with the material.

German patent applications numbers 34 42 579 and 36 16 843 disclose a process for the esterification of carboxylic acids (RCOOH) with salts of hydroxyalkanesulfonic acids, wherein the R group of the acid is a saturated and/or unsaturated hydrocarbon of 7 to 31 carbons and the esterification takes place in the presence of a consistency regulator (such as paraffin) with a salt of the formula HO—$(CH_2)_n$—$SO_3X$, where n is a number from 2–4 and X is an alkali metal or ammonium cation ($NH_4^+$). The 34 42 579 application states that the esterification is preferably carried out in a vacuum at temperatures of about 220–245 degrees C., particularly 225– 235 degrees C.

Japanese Patent 05 222395-A describes a detergent composition containing at least one weight percent of a selected acyl alkyl taurine.

Further background information may be found in Petter, P., "Fatty Acid Sulphoalkyl Amides and Esters as Cosmetic Surfactants" *International Journal of Cosmetic Science*, Volume 6, pages 249–260 (1984); Bistline, R. G. et al., "Surface Active Agents from Isopropenyl Esters: Acylation of Isethionic Acid and N-Methyltaurine" *Journal of American Oil Chemists Society*, Volumes 48, pages 657– 660 (November 1971); U.S. Pat. No. 4,234,464 to Morshauser; U.S. Pat. No. 4,092,259 to Prince; and U.S. Pat. No. 4,096,082 to Prince.

There still remains a need, however, for improved technology as applied to other classes of compounds. This invention is an extension of this technology such that N-acyltaurates can be produced by direct amidation in a cost-effective manner.

SUMMARY OF THE INVENTION

This invention comprises a method for making salts of N-alykl taurates (or taurides) of Formula I:

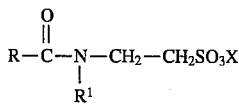

Formula I wherein: R is selected from the group consisting of $C_7$–$C_{17}$ saturated or unsaturated straight chain or branched hydrocarbyl group (preferably straight chain); $R^1$ is selected from the group consisting of hydrogen, methyl and cyclohexyl; and X is selected from the group consisting of sodium, potassium and magnesium.

For purposes of this invention, the term "hydrocarbyl group" is herein defined as an alkyl, alkenyl or alkynyl group consisting of hydrogen and carbon and having the number of carbons specified for the substituent being defined. In the case where the hydrocarbyl group is unsaturated, this will mean that there is one unsaturation and that unsaturation may occur anywhere in the group.

DETAILED DESCRIPTION OF THE INVENTION AND DESCRIPTION OF THE PREFERRED EMBODIMENTS

Compounds of Formula I may be prepared by direct amidation. A 2-aminoalkane sulfonic acid of Formula II:

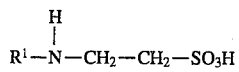

Formula II where $R^1$ has the same meaning as previously described, is reacted with a fatty acid of Formula III:

Formula III where R has the same meaning as defined above. The amidation may be done at temperatures between 180 and 205 degrees C. (195–200 degrees C. preferred), in the presence of catalytic amounts (such as, for example, from 0.1–4.0% by weight) of boric acid, and/or zinc or magnesium oxide. Temperatures in excess of 205 degrees C., result in malodorous nitrogen-based decomposition products. The addition of paraffin waxes (see the definition of paraffin wax in *Hawley's Condensed Chemical Dictionary* (11th Edition 1987), and incorporated by reference herein, lowers the viscosity so that complete condensation can be achieved. Particular types of paraffin wax which may be used with the method of this invention include synthetic and natural waxes, particularly refined paraffin waxes, and more particularly, refined paraffin waxes having a Chemical Abstracts' Service (CAS) Registry Number 64742-51-4. Thus, paraffin waxes added at levels from 0 to 20 percent (such as in an amount of 5 to 20 percent and, more particularly, in an amount of 5 to 10 percent) by weight may be added as viscosity modifiers, where increasing paraffin content allows increased conversion of alkyl taurate to N-acyl alkyltaurate.

Conversion to alkyl acyltaurate is monitored by decreasing acid number and increasing anionic activity based on two-phase methylene blue titration. Products can be quenched in water (such as up to 50 percent by weight) to produce stable aqueous dispersions of a pumpable fluid. More particular values for the amount of quenching water used are 30 to 50 percent by weight with 30 to 40 percent by weight being most preferred.

Mixed feedstocks of alkyl isethionates with alkyltaurates (e.g., sodium isethionate with sodium N-methyltaurate) may be used to synthesize in-situ products containing the acyl derivatives of said feedstocks in a "one-pot" process.

Products from said reactions can be used to manufacture a number of personal cleansing formulations (e.g., bar soap, shampoos, etc.)

The analytical techniques used for monitoring the progress of the reaction include titrimetric and gas chromatographic analyses well known by those skilled in the art to trace the decrease in fatty acid content of the mixture and the increase in the taurate content as the reaction progresses toward completion. (For examples of such analytical techniques see *Detergent Analysis—A Handbook for Cost-Effective Quality Control*, by B. M. Milwidsky and D. M. Gabriel (George Goodwin, London, 1982) incorporated by reference herein in its entirety, especially at pages 119–120, 133–134, and 255.

EXAMPLES

The following non-limiting examples are illustrative of the invention but should not be construed as limitations thereon. In the Examples, as well as elsewhere in this application, the chemical and scientific symbols have their usual and accustomed meanings and all percents are weight percents unless otherwise specified.

EXAMPLE 1

A two liter four neck reaction flask equipped with magnetic stirrer, immersion thermometer, and a distillation setup (condenser, receiver, and vacuum pump) was charged with:
340.8 g triple press stearic acid
396.8 g of 37.1% sodium N-methyl taurate solution
6.0 grams boric acid.
The flask was heated to 200 degrees C. with stirring with a subsurface nitrogen purge at 15 liter/hr, distilling off water to the distillation receiver. The reaction flask was stirred at 195–200 degrees C. for 6 hours at atmospheric pressure and 3 hours at 100 mm Hg vacuum. The mass was cooled and the resultant product was an off-white waxy solid. When ground to a powder, this powder was nearly white in color. The product (440 grams) was analyzed by a two-phase methylene blue titration as described in Mildewsky & Gabriel (cited above) and found to contain:
64.0% sodium stearyl-N-methyltaurate as active ingredient
29.5% free fatty acid
2.5% sodium N-methyltaurate
4.0% others
The conversion of sodium N-methyltaurate using this method was greater than 91%, resulting in a product of good odor, color, foaming, and lime soap dispersing characteristics.

EXAMPLE 2

The process of Example 1 was repeated except Parvan® 158 paraffin wax (22 grams) was added as a consistency regulator and process aid. The product (455 grams) was analyzed and found to contain:
65.6% sodium stearyl-N-methyltaurate as active ingredient
25.2% free fatty acid
1.5% sodium N-methyltaurate
5.0% paraffin (as determined by input not by analysis)
2.7% others
The conversion of sodium N-methyltaurate was greater than 91%, resulting in a product of good odor, color, foaming, and lime soap dispersing characteristics.

EXAMPLE 3

The process of Example 1 was repeated except coconut fatty acid (254.05 grams) was used in place of the triple pressed stearic acid. The product (355 grams) was analyzed and found to contain:
75.0% sodium cocoyl-N-methyltaurate as active ingredient
20.5% free fatty acid
1.9% sodium N-methyltaurate
2.6% others
The conversion of sodium N-methyltaurate was greater than 97%, resulting in a product of good odor, color, foaming, and lime soap dispersing characteristics.

EXAMPLE 4

The process of Example 2 was repeated except Parvan® 158 paraffin wax (17.7 grams) was added as a consistency regulator and process aid. The product (372 grams) was analyzed and found to contain:
65.7% sodium cocoyl-N-methyltaurate as active ingredient
24.9% free fatty acid
1.6% sodium N-methyltaurate
5.0% paraffin (by input)
2.8% others
The conversion of sodium N-methyltaurate was greater than 97%, resulting in a product of good odor, color, foaming, and lime soap dispersing characteristics.

EXAMPLE 5

The process of Example 3 was repeated except residual coconut fatty acid was vacuum distilled at 200 degrees C. and 3 mm Hg Vacuum. The product (302 grams) was analyzed and found to contain:
88.0% sodium cocoyl-N-methyltaurate as active ingredient
7.4% free fatty acid
2.0% sodium N-methyltaurate
2.6% others
The conversion of sodium N-methyltaurate was greater than 97%, resulting in a product of good odor, color, foaming, and lime soap dispersing characteristics.

EXAMPLE 6

Example 5 was repeated except Parvan® 158 paraffin wax (17.7 grams) was added as a consistency regulator and process aid. The product (372 grams) was analyzed and found to contain:
85.6% sodium cocoyl-N-methyltaurate as active ingredient
4.9% free fatty acid
1.7% sodium N-methyltaurate
5.0% paraffin (by input)
2.8% others
The conversion of sodium N-methyltaurate was greater than resulting in a product of good odor, color, foaming, and lime soap dispersing characteristics.

EXAMPLES 1A–6A

All of the previous Examples 1–6 were repeated using zinc oxide (0.4 grams) or magnesium oxide (0.6 grams) as catalysts. Metallic oxide catalysts produce products of reduced-malodorous compounds.

EXAMPLES 1A AND 5A

Examples 1 and 5 were repeated except that zinc oxide (0.4 grams) was used as a catalyst. The yields were approximately the same.

EXAMPLES 1B AND 5B

Examples 1 and 5 were repeated except that magnesium oxide (0.6 grams) was used as a catalyst. The yields were 15 to 20 percent lower.

What is claimed is:

1. A method for making compounds of Formula I:

wherein: R is selected from the group consisting of $C_7$–$C_{17}$ saturated or unsaturated straight chain or branched hydrocarbyl group; $R^1$ is selected from the group consisting of hydrogen, methyl and cyclohexyl; and X is selected from the group consisting of sodium, potassium and magnesium, wherein said method comprises the following steps:

(a) a direct amidation of a compound of Formula II:

with a fatty acid of Formula III: R-COOH, at a temperature between 180 degrees C. and 205 degrees C. in the presence of a catalytic amount of at least one compound selected from the group consisting of boric acid, zinc oxide and magnesium oxide;

(b) addition of up to 20 percent by weight of paraffin waxes during reaction;

(c) quenching the reaction with up to 50 percent by weight of water; and (d) forming a salt of Formula I.

2. The process of claim 1 wherein 30 to 50 percent by weight of water is used.

3. The process of claim 1 wherein 30 to 40 percent by weight of water is used.

* * * * *